United States Patent [19]

Cobia et al.

[11] Patent Number: Plant 7,571

[45] Date of Patent: Jun. 25, 1991

[54] CACTACEAE PLANT NAMED 'SANIBEL'

[76] Inventors: Barnell L. Cobia; Mark E. Cobia, both of P.O. Box 771369, Winter Garden, Fla. 34777-1369

[21] Appl. No.: 511,335

[22] Filed: Apr. 13, 1990

[51] Int. Cl.[5] ..... A01H 5/00

[52] U.S. Cl. ..... Plt./88

[58] Field of Search ..... Plt./88

*Primary Examiner*—Howard J. Locker

*Attorney, Agent, or Firm*—Roger L. Martin

[57] ABSTRACT

A new and distinct plant variety of the cactaceae family is of the type known commercially as a "Christmas Cactus" and has growth characteristics which are similar to those of the "Christmas Fantasy" variety (U.S. Plant Pat. No. 6,046), but which are nevertheless modified by a combination of characteristics that include among others: phylloclades with shorter and thicker midribs, thicker and wider wings, and thicker teeth that are also greater in number; and flowers that have longer and wider sepaloid tepals, longer and wider tube laminating tepals, shorter and wider tube forming tepals, a perianth tube with longer major and minor axis, and ovaries with longer major and minor axes.

4 Drawing Sheets

BACKGROUND OF THE INVENTION

The invention relates to a new and distinct variety of the Cactaceae family which has been named *Zygocactus truncatus* 'Sanibel' by the inventors.

Certain plant varieties of the Cactaceae family are well known in the foliage plant market and among those are those which are commonly referred to as the Christmas cactus varieties because they tend to bloom during the Thanksgiving/Christmas holiday season in the northern hemisphere.

The Christmas cactus varieties on the market have blooms which vary in color from one variety to the next as is evident from the current U.S. patent art. One of the more popular varieties sold commercially in the market t place is the variety that has been named *Zygocactus truncatus* 'Christmas Fantasy'. It forms the subject matter of U.S. Plant Pat. No. 6046.

SUMMARY OF THE INVENTION

A general objective of the invention has been to develop a new plant variety which is distinguishable from the "Christmas Fantasy" variety and which is capable of being marketed competitively therewith.

The objective has been fully realized by the development of the new plant variety hereinafter described in detail. The new plant variety was developed in a nursery located at Winter Garden, Fla. from a mutation that appeared on a specimen of the "Christmas Fantasy" variety which was under cultivation at the nursery.

Through successive propagations of cuttings taken from the mutated plant part, it has been ascertained that specimens of the new plant variety generally resemble the "Christmas Fantasy" variety but are distinguisable from this variety and from other related varieties known to the inventors by a growth habit which is evident in plant specimens of the new variety that have been propagated and grown under nursery conditions utilized in the growing of tropical plants in Winter Garden, Fla., as combining the following principal characteristics:

1. A more erect posture at maturity than the "Christmas Fantasy" variety.

2. Phylloclades which, in comparison to the "Christmas Fantasy" variety have (a) midribs with generally shorter length dimensions and generally greater thickness dimensions, (b) wings with generally greater thickness and width dimensions, and (c) teeth with generally greater thickness dimensions and in a larger number per phylloclade.
3. Flowers which, in comparison to the "Christmas Fantasy" variety, have (a) a sepaloid tepal series with generally longer length dimensions and generally greater width dimensions, (b) a tube laminating tepal series with generally longer length dimensions and generally greater width dimensions, (c) a tube forming tepal series with generally shorter length dimensions and generally greater width dimensions, (d) a perianth tube that at the throat has a generally longer major elliptical axis dimension and a generally longer minor elliptical axis dimension, and (e) ovaries with a generally longer major axis dimension at the distal end of the concavity and a generally longer minor axis dimension at the distal end of the concavity.

BRIEF DESCRIPTION OF THE DRAWINGS

The accompanying drawings serve by color photographic means to illustrate the new plant variety and wherein one sheet shows an eight (8) month old specimen which was grown from the propagation of a single phylloclade in a conventional 3½ inch plastic pot (trade designated size) found in the marketplace.

A second sheet shows an enlargement of a fully open bloom taken from the specimen shown in the first mentioned sheet.

Still another sheet show another fully open bloom together with a bloom as sectioned generally longitudinally through the perianth tube and ovary to expose the style and tamen arrangement.

The last sheet shows four branch segments taken from a specimen of the new variety and with each segment having two phylloclades and one or more buds and/or blooms, the arrangement illustrating the buds in progressive stages of maturity.

DETAILED PLANT DESCRIPTION

The following is a detailed description of the new plant variety with colors and hues, unless otherwise clearly indicated by the text, as for example, through the absence of color notations, being named in accord with the ISCC-NBS Method of Designating Colors (U.S. Dept. of Commerce, National Bureau of Standards, Circular 553), the named colors being interpreted from color notations derived by comparison with color specimens of the Munsell Book of Color. The description is further based on observations of well fertilized plants about one year old from initial propagation of a single phylloclade and which were grown under 50–75% shaded glass house nursery conditions in the Winter Garden, Fla. area and wherein temperatures range from 60°–85° F. during the winter months, from 75°–95° F. during the summer months, and are ambient during the intervening periods.

I. Name: *Zygocactus truncatus* 'Sanibel'.

II. Parentage: This variety was developed from a mutation that occurred on a plant specimen of the variety known as *Zygocactus truncatus* 'Christmas Fantasy'. (U.S. Plant Pat. No. 6,046).

III. Classification:

A. *Botanic* (*Britton and Rose, The Cactaceae, Constable and Co., Ltd., London* 1937, *vol. IV*).—(1) Family: Cactaceae. (2) Tribe: Cereeae. (3) Subtribe: Epiphyllanae. (4) Genus: Zygocactus. (5) Species: *truncatus* (Haworth) Schumann.

B. *Commercial.*—Thanksgiving/Christmas blooming cactus.

IV. Form: Epiphylic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen aging. (c) Size (at maturity) — 1. Length: Usually 28–54 mm. (Avg.=40.8 mm) (Std. dev.=6.37 mm). 2. Thickness: Usually 3–7 mm. (Avg.=4.7 mm) (Std. Dev.=1.43 mm). (d) Color (at maturity) — Usually dominated by a yellow green and/or yellowish green hue. Commonly strong yellow green (7.5 GY 6/8), moderate yellow green (7.5 GY 5/6), and/or dark yellowish green (10 GY 4/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen ageing. (d) Size (at maturity) — 1. Thickness: About 1.5–3.0 mm in the area intermediate the margin and midrib. (Avg.=2.3 mm) Std. dev.=0.44 mm). 2. Width: Usually 13–26 mm as measured from phylloclade axis to most offset lateral areole. (Avg.=17.4 mm) (Std. dev.=3.33 mm). (e) Color (at maturity) — Usually dominated by an olive green and/or yellowish green hue. Commonly moderated olive green (7.5 GY 3/4) (7.5 GY 4/5)(7.5 GY 4/4) and/or dark yellowish green (10GY 4/6)(10 GY 3/4). (4) Teeth: (a) Shape — 1. General: Generally flattened and tapered along the margins and from the wing insertion to an apex having a hyaline, single cell, pointed spine with non-predictable bending. 2. Adaxial margin: Usually straight to convex. 3. Abaxial margin: Usually straight to concave. (b) Orientation — Usually project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 1.0–2.5 mm in center area. (Avg.=1.5 mm) (Std. dev.=0.46 mm). 2. Areole to apex dimension (adaxial marginal side): Usually 2–15 mm in the upper quadrants of the phylloclades. (Avg.=7.1 mm) (Std. dev.=3.71 mm). (f) Number — Usually 7–8 per phylloclade. (g) Color — Usually dominated by an olive green and/or yellowish green hue. Commonly moderate olive green (7.5 GY 4/6) (7.5 GY 4/4) and/or dark yellowish green (10 GY 4/6) (10 GY 3/4). (5) Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axils of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds: Unarmored, ovoid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and tube forming series off united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 4–6. (5) Size (at full bloom): (a) Length (base-tip dimension) — Usually less than 13 mm. (Avg.=7.4 mm) (Std. dev.=3.09 mm). (6) Color (at full bloom): Varies from the outer members to the inner members with the smallest outer whorl tepals usually having a continuous filed that in color is dominated by a yellow green hue. The inner whorl tepal members have marginal blade and blade center field areas that in color are dominated by yellowish pink hues that project proximally to merge with color in the basal area that projects distally and is commonly white or dominated by a yellow green hue. Commonly light yellowish pink (near 5 YR 8/4) (near 2.5 YR 8/4) (Near 10 R 8/4), and/or moderate yellowish pink (near 5 YR 8/4) (near 2.5 YR 8/4) (near 10 R 8/4) (2.5 YR 7/6) in marginal and center field areas of the inner whorl members, strong yellow green (5 GY 7/8) (5 GY 7/10) (2.5 GY 7/8) in the basal areas of the inner whorl members, and strong yellow green (5 GY 7/8) (5GY 7/10) (2.5 GY 7/8) in the continuous field of the outer whorl members. (7) Orientation: Erect to recurve at full bloom.

C. *Tube laminating series.*—(1) General: Tepals inserted on ovary and becoming basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Margins are entire to fimbriate or erose in apex areas. Teeth are irregular and sparse and appear mainly in apex areas. (3) Texture: Succulent and glabrous outer whorl members and grading inwardly to silken blades with slightly fleshy basal areas. (4) Number: Usually 7–10 tepals. (5) Size (at full bloom): (a) Length (base-tip dimension) — Usually 14–58 mm. (Avg.=29.9 mm) (Std. dev.=12.28 mm). (b) Width (maximum) — Usually 9–20 mm. (Avg.=15.8 mm) (Std. dev.=2.67 mm). (6) Color (at full bloom): (a) General — Tepals with basal areas that in color are white and/or dominated by a yellow green hue immediately above the insertion, and with marginal blade and blade center field areas that in color are dominated by yellowish pink, orange, and/or reddish orange hue(s) which merge with the distally extending basal area colors. (b) Basal area — Commonly white (2.5 YR 9/0) in the inner whorl members, and light yellow green (5 GY 9/6) and/or brilliant yellow green (5 GY 8/8) in the outermost members of the whorl. (c) Blade area — Commonly light yellowish pink (near 2.5 YR 8/4) (near 10 R 8/4), moderate yellowish pink (near 2.5 YR 8/4) (near 10 R 8/4), moderate orange (2.5 Y R 7/8), strong yellowish pink (10 R 7/8), and/or moderate reddish orange (10R6/10) in the marginal and center field areas. (7) Orientation: Perpendicular to recurve with revolute tendencies.

D. *Tube forming series.*—(1) General: Tepals basally united to form hollow perianth tube that is inserted on ovary and equipped at its throat with an irregular carina (keel). (2) Shape: (a) Perianth tube — Elongated and ellipsoidal in cross section with the major ellipsoidal axis usually generally normal to the plane of the supporting phylloclade. (b) Blades — Nearly zygomorphic and spatulate with acute tips and entire to fimbriate or erose margins having sparse irregular teeth mainly in the apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 7–9 tepals. (5) Size (at full bloom): (a) Perianth tube — 1. Length (base-keel): Usually 32–41 mm along tube axis. (Avg.=36.3 mm) (Std. dev.=3.31 mm). 2. Major axis: Usually 9–13 mm at throat interior. (Avg.=11.5 mm) (Std. dev.=1.41 mm). 3. Minor axis: Usually 7–10 mm at throat interior. (Avg.=8.4 mm) (Std. dev.=1.09 mm). (b) Blades — 1. Length (keel-tip): Usually 27–32 mm. (Avg.=29.4 mm) (Std. dev.=1:21 mm). 2. Width (maximum): Usually 13–20 mm. (Avg.=15.9 mm) (Std. dev.=1.21 mm). (6) Color (at full bloom): (a) Perianth tube — A basic field that is translucent white with longitudinally extending, randomly arranged striations or streaks that in color are commonly purplish white (5 RP 9/1). The basic field is translucent and commonly white (5 RP 9/0). (b) Blades — Marginal blade and blade center field areas that are nearly uniform in color distally of the keel and dominated by yellowish pink and/or orange hues. Commonly yellowish pink (near 10 R 8/4), moderate yellowish pink (near 10 R 8/4), strong yellowish pink (10 R 7/8), moderate orange (near 2.5 YR 7/100 (2.5 YR 7/8) and/or strong orange (near 2.5 YR 7/10). (c) Carina (keel) — Color dominated by a purplish pink hue. Commonly deep purplish pink (5 RP 6/10). (7) Orientation: Acute to recurve with revolute tendencies.

E. *Androecium (stamens).*—(1) General: Numerous exserted and diadelphous stamens with one group having filaments basally fused to the perianth tube and another group having filaments basally united to form a nectary housing, thin annulus around the style and which is provided with a thin, deflexed, irregular, toothed margin or ruffle at the throat of the annulus. (2) Stamen number: (a) Tube attached group — Usually 67–91. (b) Basally united group — Usually 15–20. (3) Filaments: (a) General — Translucent with anther connective. (b) Shape — Long, slender, terete. (c) Texture — Glabrous and capillaceous. (d) Color — Usually translucent and white over entire length. (e) Size (at full bloom) — 1. Length: (a) Tube attached group — Usually 25–56 mm. (Avg.=43.9 mm) (Std. dev.= 7.68 mm). (b) Basally united group — Usually 30–50 mm. (Avg.=42.2 mm) (Std. Dev.=5.47 mm). (c) Diameter: Usually about 0.75 mm at insertion and tapering to about 0.50 mm at distal end. (4) Anthers: (a) General — Adnate with four longitudinally dehiscent pollen sacs and connective inserted at end. (b) Shape — Elongated. (c) Texture — Waxy. (d) Color (before dehiscence) — Dominated by a greenish yellow hue. Commonly pale greenish yellow (10Y 9/4) and/or light greenish yellow (10 Y 9/6). (e) Sterility — Sterile.

F. *Gynoecium (pistil)*.—(1) General: Exserted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a reddish purple hue and progressively varying in color from the basal to the distal ends. Commonly strong reddish purple (2.5 RP 5/10) (2.5 RP 4/10) at basal end and deep reddish purple (2.5 RP 3/10) at distal end. (e) Size (at full bloom) — 1. Length: Usually 49–55 mm. (Avg.=51.7 mm) (Std. dev.=2.01 mm). 2. Diameter: Usually 1.0–1.5 mm intermediate opposite ends. (Avg.=1.3 mm) (Std. dev. 0.25 mm). (3) Stigma: (a) General — Exserted and erect with usually 6–8 inner marginal adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by a reddish purple hue. Commonly light reddish purple (2.5 RP 6/8) and/or strong reddish purple (2.5 RP 5/10). (e) Size — 1. Length: Usually 4–7 mm along inner margins. (Avg.=5.8 mm) (Std. dev.=1.35 mm). (4) Ovary: (a) General — inferior with thin epidermis and usually 5–7 carpules with numerous ovules. (b) Shape — Terete to ovoid and generally broadening from insertion to floral end. Ribbed single concavity with inserted style. (c) Texture — Succulent with glabrous thin outer epidermis. (d) Color — Usually dominated by a yellow green hue and commonly moderate yellow green (2.5 GY 5/6) (5 GY 5/6) and/or strong yellow green (2.5 GY 6/8) (5 GY 6/8). (e) Size — 1. Length: Usually 8–10 mm from insertion to cavity base. (Avg.=8.6 mm) (Std. dev.=0.77 mm). 2. Major axis: Usually 9–12 mm at distal end of concavity. (Avg.=10.6 mm) (Std. dev.=1.13 mm). 3. Minor axis: Usually 8–10 mm at distal end of concavity. (Avg.=9.1 mm) (Std. dev.=0.90 mm).

VIII. Growth habit: Erect.

GENERAL DESCRIPTION OF A PLANT SPECIMEN OF AND FLOWER FROM THE "SANIBEL" VARIETY

The Plant

Age of plant specimen: Eight (8) months from initial propagation of single phylloclade.

Branches developed from propagated phylloclade: Two (2).

Total number of new phylloclades produced: Eight (8).

General:

| Branch No. | No. of Phylloclades | Max. Length | No. of Tips |
|---|---|---|---|
| 1 | 3 | 47 mm | 1 |
| 2 | 5 | 46 mm | 2 |

Midribs:

| Branch No. | Length (avg.) | Thickness (avg.) |
|---|---|---|
| 1 | 44.7 mm | 4.5 mm |
| 2 | 43.6 mm | 4.3 mm |

Wings:

| Branch No. | Center Thickness (avg.) | Max. Width (avg.) |
|---|---|---|
| 1 | 2.3 mm | 16.0 mm |
| 2 | 2.6 mm | 15.6 mm |

Teeth:

| Branch No. | Teeth per Phylloclade (avg.) | Center Thickness (avg.) | Areole to Apex Length (avg.) |
|---|---|---|---|
| 1 | 7.7 | 1.3 mm | 5.8 mm |
| 2 | 7.4 | 1.4 mm | 6.1 mm |

Phylloclade color: Strong yellow green (7.5 GY 6/8), moderate yellow green (7.5 GY 5/6), dark yellowish green (10 GY 4/6) (10 GY 3/4), moderate olive green (7.5 GY 3/4) (7.5 GY 4/4) (7.5 GY 4/6).

THE FLOWER

The following is a general description of a flower of the new plant variety and which bloomed in December on an eight (8) month old plant specimen grown under shaded greenhouse nursery conditions in Winter Garden, Fla., USA.

No of buds and blooms on plant specimen: three (3).

Bloom life: Nine (9) days.

Sepaloid series of tepals:

1. *Number of tepals*.—5.
2. *Size (at full bloom)*.—(a) Maximum base-tip dimension: 12 mm. (b) Minimum base-tip dimension: 4 mm. (c) Maximum width dimension: 12 mm.
3. *Color (at full bloom)*.—Strong yellow green (5 GY 7/8) (5 GY 7/10) (2.5 GY 7/8) in continuous field of outer whorl members of small tepals. Light yellowish pink (near 5 YR 8/4) (near 10 R 8/4) (near 2.5 YR 8/4) and moderate yellowish pink (near 5 YR 8/4) (near 10 R 8/4) (2.5 YR 8/4) in marginal and center field areas and strong yellow green (5 GY 7/8) (5 GY 7/10) (2.5 Gy 7/8) in the basal areas of the inner whorl members.

Tube laminating series of tepals:

1. *Number of tepals*.—9.
2. *Size (at full bloom)*.—(a) Maximum base-tip dimension: 55 mm. (b) Minimum base-tip dimension: 16 mm. (c) Maximum blade width: 18 mm. (d) Minimum blade width: 15 mm.
3. *Color*.—Light yellowish pink (near 2.5 YR 8/4) (near 10 R 8/4), moderate yellowish pink (near 2.5 YR 8/4) (near 10 R 8/4), moderate orange (2.5 YR 7/8), strong yellowish pink (10R 7/8), and/or moderate reddish orange (10 R 6/10) in marginal and center field areas of the blades and white (2.5 YR 9/0) in the basal areas of the blades.

Tube forming series of tepals:

1. *Number of tepals*.—Eight (8).
2. *Size (at full bloom)*.—(a) Perianth tube: (1) Length (base to keel) — 38 mm along tube axis.

(2) Major axis — 12 mm at throat interior. (3) Minor axis — 8 mm at throat interior. (b) Blades: (1) Maximum length (keel-tip) — 31 mm. (2) Minimum length (keel-tip) — 28 mm. (3) Maximum blade width — 19 mm. (4) Minimum blade width — 16 mm.

3. *Color.*—(a) Perianth tube: A major field of white (5 RP 9/0) with random striations of purplish white (5 RP 9/1). (b) Blades: White (5 RP 9/0) in basal areas of blades and yellowish pink (near 10 R 8/4), moderate yellowish pink (near 10 R 8/4), strong yellowish pink (10 R 7/8), moderate orange (near 2.5 YR 7/10) (2.5 YR 7/8) in marginal and center field areas of the blades.

Androecium:

1. *Stamen number.*—(a) Tube attached group: 87. (b) Basally united group: 17.
2. *Filaments.*—(a) Color: Translucent and white over entire length. (b) Size (at full bloom): (1) Length — a. Tube Attached Group: 48 mm (avg.). b. Basally United Group: 42 mm (avg.). (2) Diameters: About 0.50 mm intermediate the opposite ends.
3. *Anthers.*—(a) Color (before dehiscing): Pale greenish yellow (10 Y 9/4).

Gynoceium (pistil):

1. *Style.*—(a) Color; Strong reddish purple (2.5 RP 4/10) in basal area and deep reddish purple (2.5 RP 3/10) in distil area. (b) Size (at full bloom): (1) Length — 51 mm. (2) Diameter — 1.0 mm intermediate the opposite ends.
2. *Stigma.*—(a) Color: Light reddish purple (2.5 RP 6/8), strong reddish purple (2.5 RP 5/10). (b) Size: 6 mm (avg.) lobe length.
3. *Ovary.*—(a) Color: Moderate yellow green (2.5 GY 5/6) (5 GY 5/6), strong yellow green (2.5 GY 6/8) (5 GY 6/8). (b) Size (at full bloom): (1) Length (insertion to concavity base) — 10 mm. (2) Major axis — 11 mm at distal end of concavity. (3) Minor axis — 8 mm at distal end of concavity.

We claim:

1. A new and distinct plant variety of the Cactaceae family as shown and described and which is mainly distinguished from its antecedents and known related varieties by growth characteristics that are similar to those of the "Christmas Fantasy" variety but as modified by the combination of the following characteristics:

(1) A more erect posture at maturity than the "Christmas Fantasy" variety;

(2) Phylloclades which, in comparison to the "Christmas Fantasy" variety have (a) midribs with generally shorter length dimensions and generally greater thickness dimensions, (b) wings with generally greater thickness and width dimensions, and (c) teeth with generally greater thickness dimensions and in a larger number per phylloclade; and (3) Flowers which, in comparison to the "Christmas Fantasy" variety, have (a) a sepaloid tepal series with generally longer length dimensions and generally greater width dimensions, (b) a tube laminating tepal series with generally longer length dimensions and generally greater width dimensions, (c) a tube forming tepal series with generally shorter length dimensions and generally greater width dimensions, (d) a perianth tube that at the throat has a generally longer major elliptical axis dimension and a generally longer minor elliptical axis dimension, and (e) ovaries with a generally longer major axis dimension at the distal end of the concavity and a generally longer minor axis dimension at the distal end of the concavity.

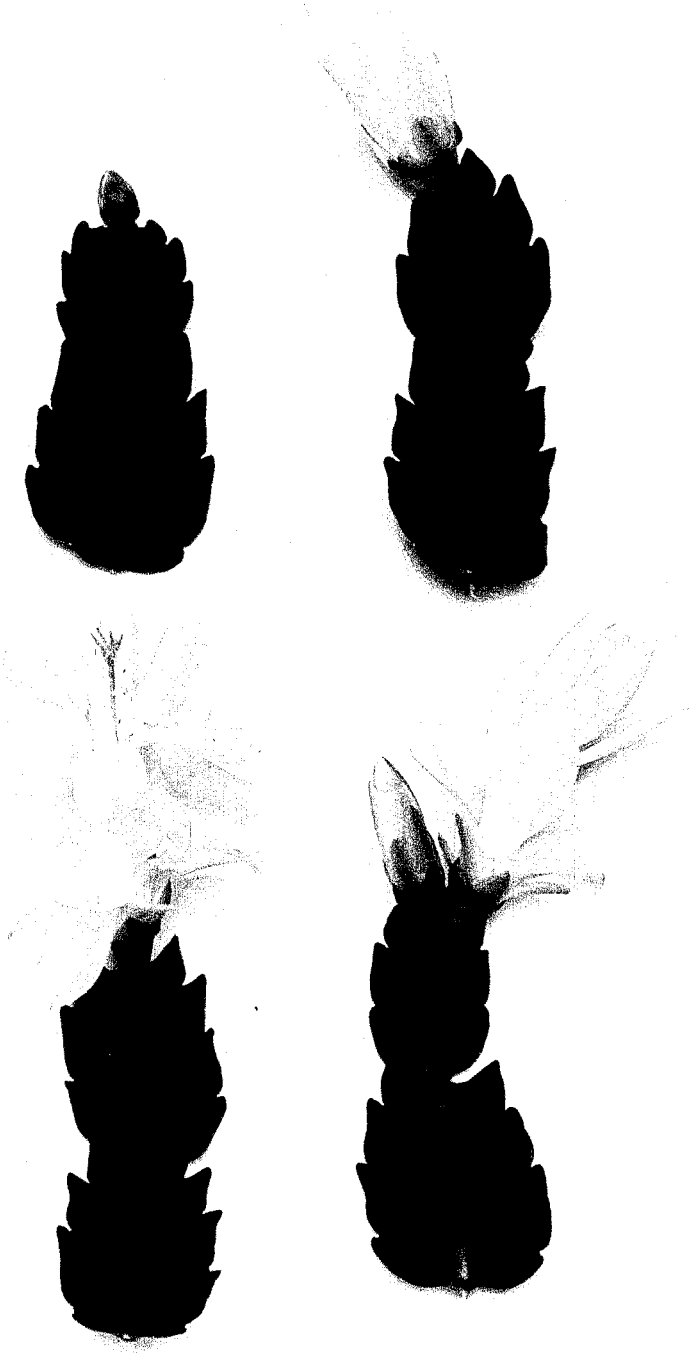

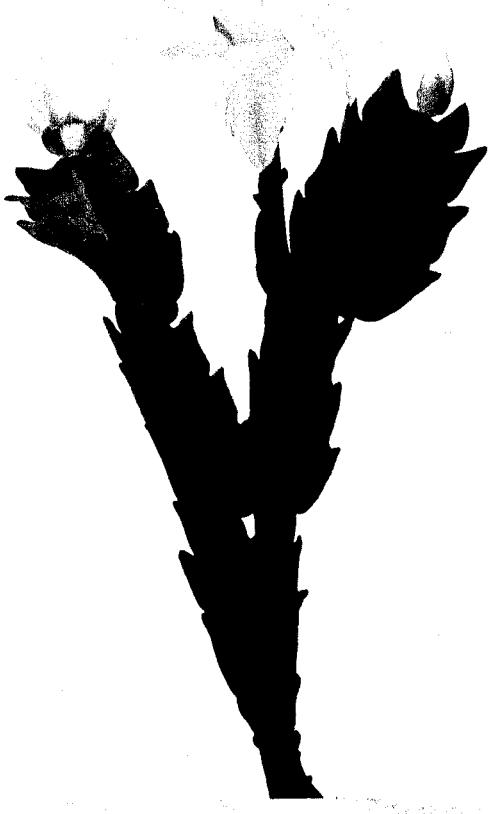

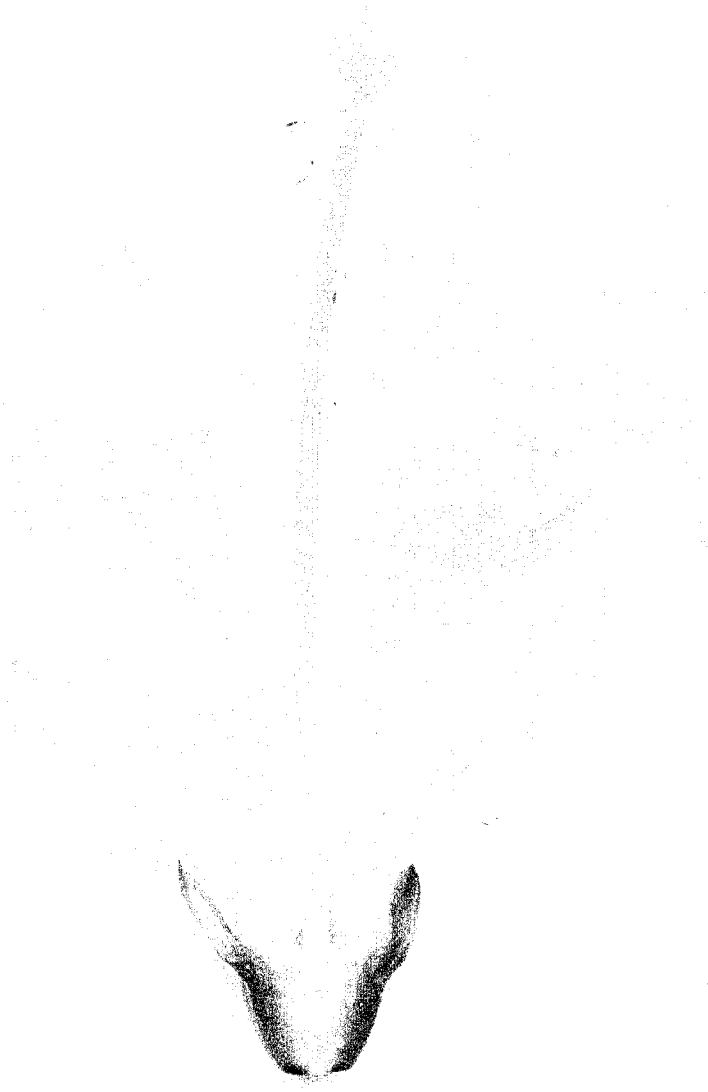

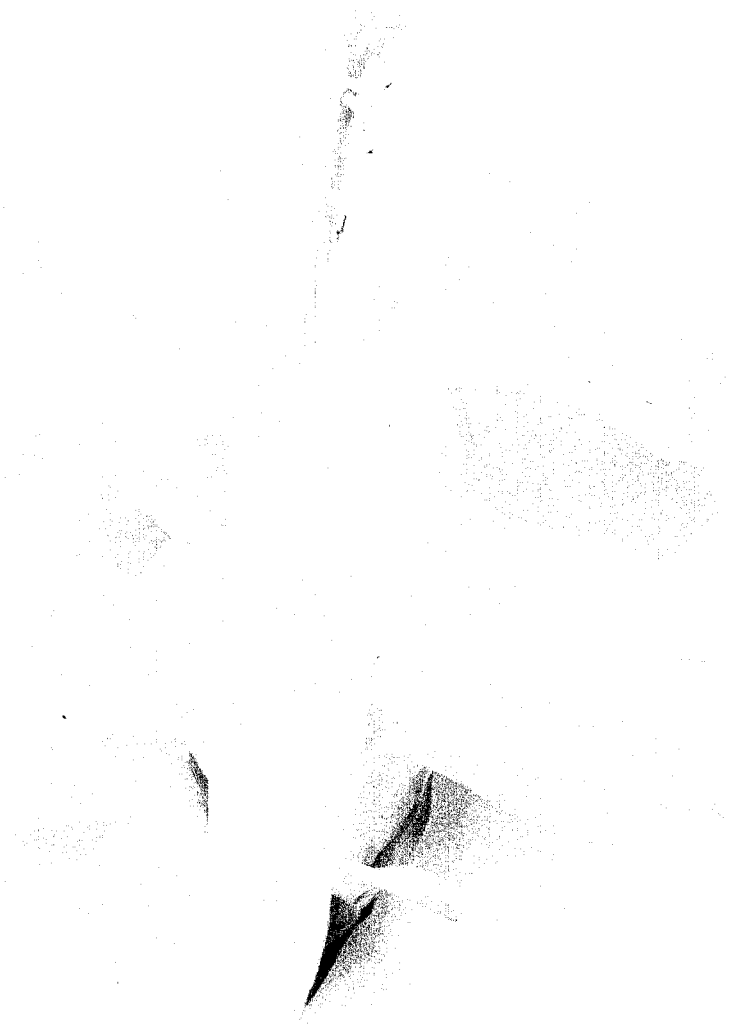

* * * * *